United States Patent
Dick et al.

(10) Patent No.: US 12,419,321 B2
(45) Date of Patent: Sep. 23, 2025

(54) CASTING COMPOUND AND PROCESS FOR THE PRODUCTION OF GELATIN PRODUCTS

(71) Applicant: GELITA AG, Eberbach (DE)

(72) Inventors: Eberhard Dick, Neckargemünd (DE); Sonja Göttling, Heppenheim (DE); Anna Leitheim, Mosbach (DE); Alexander Raab, Neckarsteinach (DE); Holger Brack, Rümmelsheim (DE)

(73) Assignee: GELITA AG, Eberbach (DE)

( * ) Notice: Subject to any disclaimer, the term of this patent is extended or adjusted under 35 U.S.C. 154(b) by 962 days.

(21) Appl. No.: 16/006,102

(22) Filed: Jun. 12, 2018

(65) Prior Publication Data

US 2018/0289032 A1     Oct. 11, 2018

Related U.S. Application Data

(63) Continuation of application No. PCT/EP2016/079388, filed on Dec. 1, 2016.

(30) Foreign Application Priority Data

Dec. 16, 2015 (DE) .......................... 102015121923.9

(51) Int. Cl.
  *A23G 3/42* (2006.01)
  *A23G 3/34* (2006.01)
  *A23G 3/44* (2006.01)
  *A23L 29/281* (2016.01)

(52) U.S. Cl.
  CPC ............. *A23G 3/42* (2013.01); *A23G 3/0027* (2013.01); *A23G 3/44* (2013.01); *A23L 29/284* (2016.08); *A23V 2002/00* (2013.01)

(58) Field of Classification Search
  CPC .......... A23G 3/42; A23G 3/44; A23G 3/0014; A23G 3/0027; A23L 29/284; A23L 29/281; A23V 2002/00; A61P 3/02
  USPC ....................................................... 426/289
  See application file for complete search history.

(56) References Cited

U.S. PATENT DOCUMENTS

| | | | |
|---|---|---|---|
| 5,229,164 A | 7/1993 | Pins et al. | |
| 2003/0064074 A1* | 4/2003 | Chang | A61K 8/65 424/184.1 |
| 2004/0013732 A1* | 1/2004 | Farber | A23G 3/346 424/488 |
| 2006/0024390 A1* | 2/2006 | Schauss | A61K 36/889 424/727 |
| 2007/0148292 A1 | 6/2007 | Royo et al. | |
| 2008/0299622 A1* | 12/2008 | Paulson | C12P 7/06 435/99 |
| 2009/0285963 A1 | 11/2009 | Dick et al. | |
| 2013/0071516 A1* | 3/2013 | Elejalde | A23G 4/20 426/5 |
| 2014/0127375 A1* | 5/2014 | Cao | A23G 3/42 426/548 |
| 2014/0287123 A1 | 9/2014 | Dick et al. | |
| 2015/0216199 A1 | 8/2015 | Porter et al. | |
| 2015/0232534 A1* | 8/2015 | Oesser | A61P 3/02 514/16.9 |
| 2015/0282508 A1* | 10/2015 | Capdepon | A23C 9/1526 426/570 |
| 2017/0342130 A1* | 11/2017 | Olijve | C07K 14/78 |

FOREIGN PATENT DOCUMENTS

| | | |
|---|---|---|
| BE | 898 236 A1 | 3/1984 |
| DE | 10 2007 007 307 A1 | 8/2008 |
| DE | 10 2011 056 018 A1 | 6/2013 |
| EP | 2 724 623 A1 | 4/2014 |
| WO | WO 97/41738 A1 | 11/1997 |
| WO | WO 98/12935 A1 | 4/1998 |
| WO | WO 2004/056976 A2 | 7/2004 |
| WO | WO 2005/094782 A1 | 10/2005 |
| WO | WO 2009/072817 A2 | 6/2009 |
| WO | WO 2012/006215 A1 | 1/2012 |

OTHER PUBLICATIONS

NPL Badii et al. (Food Hydrocolloids , vol. 20: pp. 630-640, 2006). (Year: 2006).*
NPL Kim et al. (in J Agric. Food Chem. vol 49: 2992-2997, 2001) (Year: 2001).*
NPL Dry Matter Calculator (Under Feline Nutrition, entitled Dry matter basis online calculator: Retrieved on Nov. 2020) (Year: 2020).*
NPL "Hollow moulds" retrieved on Nov. 18, 2020. (Year: 2020).*
NPL granulated sugar (Retrieved on May 28, 2021). (Year: 2021).*
NPL Total dry matter (Retrieved on Jun. 1, 2021). (Year: 2021).*
NPL Yang et al. (in J. Food Sci. Nutr. vol 2 (3) , pp. 263-268, 1997). (Year: 1997).*
NPL glucose syrup (Retrieved on Oct. 1, 2021). (Year: 2021).*
Google search Report [containing NPL Yang et al. : See p. 2 third NPL reference) (Retrieved on Sep. 16, 2021) (Year: 2021).*

(Continued)

*Primary Examiner* — Erik Kashnikow
*Assistant Examiner* — Bhaskar Mukhopadhyay
(74) *Attorney, Agent, or Firm* — Leydig, Voit & Mayer, Ltd.

(57) ABSTRACT

A casting compound for the production of gelatin products comprises a homogenous aqueous solution having: 4% to 16% by weight of gelatin having a molecular weight determined by gel chromatography of at least 130 kDa, where the proportion of the gelatin having a molecular weight exceeding 130 kDa is at least 35% by weight, 6% to 76% by weight of one or more sugar alcohols; 0% to 50% by weight of glucose syrup having a viscosity of less than 800 mPas, measured at a dry matter content of 80% by weight and a temperature of 50° C.; and 0% to 50% by weight of sucrose, where the glucose syrup and the sugar alcohol(s) together make up 25% to 76% by weight of the aqueous solution, and where the aqueous solution has a dry matter content of at least 78% by weight and/or a water activity (aw value) of less than 0.75.

14 Claims, No Drawings

(56) References Cited

OTHER PUBLICATIONS

NPL Cai, C-F et al. (in entitled "Antioxidant and Functional Properties of Collagen Hydrolysates from Spanish Mackerel Skin as Influenced by Average Molecular Weight " in Molecules 2014, 19, 11211-11230). (Year: 2014).*
NPL sugar syrup (Retrieved on Apr. 5, 2022). (Year: 2022).*
Google search result (Result retrieved above NPL sugar syrup from article 2, first page e.g. Owl software . . . article). (retrieved on Apr. 6, 2022). (Year: 2022).*
Additionally, Google search was performed and retrieved on Apr. 6, 2022. (Year: 2022).*
NPL Netter et al. (LWT vol. 132, Oct. 2020). (Year: 2020).*
International Bureau, International Search Report in International Application No. PCT/EP2016/079388, mailed Feb. 28, 2017.
Schrieber et al., "Gelatine Handbook—Theory and Industrial Practice," *Wiley-VCH*, pp. 48-54, 113-114, 163-172 (2007).
International Bureau, English translation of International Preliminary Report on Patentability in International Application No. PCT/EP2016/079388, mailed Jun. 28, 2018.

* cited by examiner

CASTING COMPOUND AND PROCESS FOR THE PRODUCTION OF GELATIN PRODUCTS

CROSS-REFERENCE TO RELATED APPLICATIONS

This patent application is a Continuation of International Patent Application No. PCT/EP2016/079388, filed Dec. 1, 2016, which claims the benefit of German Patent Application No. 10 2015 121 923.9, filed Dec. 16, 2015, which are each incorporated by reference.

FIELD OF THE INVENTION

The present invention relates to a casting compound for producing gelatin products.

The invention also relates to a method for producing gelatin products using this casting compound, and also to the gelatin products produced therefrom.

BACKGROUND OF THE INVENTION

The generic term "gelatin products" as used hereinafter includes on the one hand popular sugar confectionary products characterised primarily by a more or less elastic texture. Besides the gelatin, various sugar types and/or sugar substitutes form the main constituent of these products, which can be referred to in the broadest sense as gummy sweets, and in particular are known in the form of gummy bears or fruit gums.

On the other hand, such gelatin products are also used as chewable tablets in the field of dietary supplements and medicinal products, wherein various nutrients (for example vitamins, minerals or peptides) and/or pharmaceutical active substances are added to the basic recipe. The sugar content can be reduced in this case, wherein the transition from confectionery to dietary supplements is rather blurred. Gummy sweets or chewable tablets enriched with various additives or active substances are offered for example as what are known as "fortified gummies."

The previously used production method for such gelatin products is known as the mogul technique. In this method, a hot casting compound having a water content of approximately 25 wt % and containing the gelatin, the sugar and the other constituents dissolved in water is poured into hollow moulds formed from a starch moulding powder. The hollow moulds are produced beforehand by pressing a positive mould into the smooth surface of a flat tray filled with dry starch powder. Once the hollow moulds have been filled, the starch powder trays are stored for between 24 and 72 hours in a climatic chamber. During this time, the casting compound in the hollow moulds cools, which causes the cast article to set. In parallel hereto, some of the water is absorbed by the starch moulding powder, such that a drying process takes place, wherein the finished gelatin products generally have a water content of approximately 20 wt % or less. The powder trays are then emptied, and the starch moulding powder is separated from the gelatin products by means of sieving and is re-used after having been dried. The gelatin products are treated with a release agent ("lubrication") in order to prevent any sticking, and are packaged.

The use of starch moulding powder for the production of the hollow moulds is associated with various disadvantages. Due to the long drying time (24 to 72 hours) of the gelatin products cast in starch moulding powder using the known recipes, large drying chambers and a very high number of moulding powder trays are required in the case of suitably high-performance mogul plants, which cast up to 35 powder trays per minute. The space requirement and the necessary investment for climate control, moulding powder trays, starch driers, and not least the starch moulding powder are therefore considerable. The contamination of the production areas with starch powder, which cannot be completely avoided in spite of constant cleaning, is also problematic.

A further disadvantage of the mogul method is the risk of cross-contamination in the event of a product change, since contaminations of the previously produced product always remain in the starch and can be introduced into the new product with continuous re-use of the starch moulding powder. This problem could be avoided only by discarding all of the starch moulding powder prior to each product change, however this would be completely uneconomical.

The described disadvantages of the known production method are extremely critical in particular for the production of pharmaceutical products. With regard to hygiene (contamination by starch dust) and purity (cross-contamination), the mogul technique does not meet the demands of the pharmaceutical standards (GMP guidelines) and thus severely restricts the fields of application of gummy sweets or chewable tablets as medicinal dosage forms.

The use of solid, re-usable hollow moulds (in particular made of plastics material) for the casting of gelatin products of this type previously failed for economical and technical reasons. Such methods are indeed known for the production of sugar confectionary products based on other, rapidly setting hydrocolloids (such as pectin), which allow a low viscosity of the casting compound. However, the sensory properties of these products differ significantly, and therefore they are not considered by consumers to constitute an alternative to gelatin products.

It is not possible to dry the known gelatin-based casting compounds in solid hollow moulds, since water would be able to escape only via the open upper side. This is not sufficient for complete and homogeneous drying. Changes to the recipe are very difficult, since different, sometimes contrary basic conditions must be observed: On the one hand, the rheological properties of the casting compound must be suitable for the casting process, and on the other hand, the end product should have the typical texture of gelatin products expected by the consumer.

BRIEF SUMMARY OF THE INVENTION

The object of the present invention is therefore to provide a casting compound for producing gelatin products which is suitable for casting in solid hollow moulds.

This object is achieved in accordance with the invention by a casting compound of the type mentioned in the introduction, which comprises a homogeneous aqueous solution containing the following constituents:
- 4 to 16 wt % of gelatin having a mean molecular weight, determined by gel chromatography, of at least 130 kDa, preferably at least 145 kDa, wherein the proportion of the gelatin having a molecular weight of more than 130 kDa is at least 35 wt %, preferably at least 45 wt %;
- 6 to 76 wt % of one or more sugar alcohols;
- 0 to 50 wt % of glucose syrup with a viscosity of less than 800 mPa·s, preferably less than 700 mPa·s, measured with a dry matter content of 80 wt % and at a temperature of 50° C.; and
- 0 to 50 wt % of sucrose,
- wherein the glucose syrup and the sugar alcohol(s) together make up 25 to 76 wt % of the aqueous solution, and wherein the aqueous solution has a dry matter content of at least 78 wt % and/or a water activity ($a_w$ value) of less than 0.75.

It has surprisingly been found that, during the cooling after the pouring, the casting compound according to the invention is able to achieve the texture and consistency typical for gelatin products merely by the setting of the gelatin, without the need for significant drying, i.e. a release of water, for this purpose. This is made possible by a casting compound which substantially already has the same low water content as the gelatin products to be produced.

In spite of the higher dry matter content compared to the prior art, the casting compound has, on account of its components, rheological properties which allow processing in the conventional way. On the one hand, a sufficiently low viscosity of the hot casting compound and, on the other hand, a rapid solidification of the system during cooling are decisive factors. Only in this way can undesirable phenomena such as filament formation and/or air inclusions be avoided alongside good mouldability.

Due to these properties, the casting compound according to the invention can be cast, in the case of production of gelatin products, in solid hollow moulds in particular made of a plastics material, such as silicone. Besides the advantages resulting here from the omission of the previously used starch moulding powder, this also leads to a significant shortening of the production method, since the casting compound according to the invention is generally solid enough in less than just 60 minutes to be able to be demoulded without excessive adhesion. By contrast, the products cast using the known recipes in starch moulding powder require between 24 and 72 hours to dry. The casting compound according to the invention thus leads, with the same quantities per unit of time, to a significantly reduced space requirement for the cooling gummy sweets, which significantly lowers the investment for the hollow moulds and the storage space for the drying, which is no longer required, and also the operating costs (no starch drying or climate control of the storage areas).

DETAILED DESCRIPTION OF THE INVENTION

The casting compound according to the invention achieves the stated object by means of the cooperation of the contained components within the above-mentioned quantity ranges. An essential feature of the invention is the selection of a high-molecular gelatin with a mean molecular weight, determined by gel chromatography, of at least 130 kDa, wherein the proportion of the gelatin having a molecular weight above 130 kDa is at least 35 wt %. Such gelatins can be obtained from various collagen-containing materials, in particular from connective tissue or bones of pigs, cattle, poultry or fish.

Flavourings, colourings and/or acidifiers can be contained as further components in the casting compound, in particular in the homogeneous aqueous solution, wherein the typical quantity proportions of such additives are known from the prior art. The conventional edible acids, preferably citric acids, are used as acidifier.

The casting compound according to the invention, in addition to the above-described components, can also contain further constituents, provided these do not have a negative effect on the specified advantageous properties of the casting compound. In a preferred embodiment, the casting compound comprises one or more nutrients and/or pharmaceutical active substances, wherein these can be dissolved or dispersed in the homogeneous aqueous solution depending on the degree of solubility. In the first case, the proportion of such components is preferably less than 45 wt %, more preferably less than 35 wt %.

Preferred nutrients in the casting compound according to the invention are selected from vitamins, minerals, plant extracts, and peptides, in particular collagen peptides (collagen hydrolysate). The corresponding gelatin products can be enriched confectionery products (fortified gummies) or dietary supplements.

The casting compound according to the invention can also be used for the production of medicinal products (for example in the form of chewable tablets), and in this case contain pharmaceutical active substances, for example painkillers such as acetylsalicylic acid, paracetamol, or ibuprofen. The suitability of the casting compound for the use of solid hollow moulds, in contrast to the mogul technique, makes it possible to observe the hygiene standards applicable in this area (GMP guidelines).

The gelatin can be contained in the aqueous solution in a proportion of from 4 to 16 wt %, wherein a proportion of from 5 to 12 wt % is preferred, in particular from 6 to 10 wt %. Within this range, gelatin products that have a typical texture, in particular a high elasticity, are obtained.

Glucose syrup and sucrose can be contained in the aqueous solution in a proportion of, in each case, up to 50 wt %. However, these components can also be omitted for the production of sugar-free products and can be compensated for by a higher proportion of sugar alcohols.

With use of glucose syrup, this preferably has a viscosity of less than 800 mPa·s, more preferably of less than 700 mPa·s, measured with a dry matter content of 80 wt % and at a temperature of 50° C. The glucose syrup is conveniently a highly hydrolysed glucose syrup with a dextrose equivalent of 50 or more, preferably of 60 or more.

Apart from in the case of sugar-free products, the aqueous solution preferably contains a proportion of from 8 to 40 wt % of glucose syrup, more preferably from 15 to 28 wt %.

Sucrose, that is to say commercially available sugar, is preferably contained in the aqueous solution (apart from in the case of sugar-free products) in a proportion of from 15 to 45 wt %, more preferably from 20 to 40 wt %.

The aqueous solution also comprises one or more sugar alcohols in a proportion of from 6 to 76 wt %, preferably from 10 to 30 wt %. Due to the use of these sugar substitutes, the quantity of sugar and/or glucose syrup can be reduced on the one hand, and on the other hand the sugar alcohols also contribute to the favourable rheological properties of the costing compound.

The sugar alcohol(s) is/are preferably selected from sorbitol, mannitol, xylitol, erythritol and glycerol, wherein sorbitol is particularly preferred.

In accordance with a variant of the invention, the homogeneous aqueous solution also comprises one or more further hydrocolloids, in particular pectin, in order to modify the properties of the gelatin products (for example temperature stability and elasticity). The proportion of further hydrocolloids is preferably from 0.1 to 10 wt %, in particular from 0.2 to 5 wt %.

The casting compound according to the invention is suitable, as described above, for the production of gelatin products by casting in solid hollow moulds, in particular made of a plastics material.

The present invention therefore also relates to a method for producing gelatin products, said method comprising the following steps:
producing a casting solution according to the invention;
pouring the casting solution at a temperature of 80° C. or more into solid hollow moulds;
cooling the casting solution in the hollow moulds in order to obtain the gelatin products; and
removing the gelatin products from the hollow moulds.

The cooling of the casting solution in the hollow moulds is performed preferably within a period of time of less than 60 min., more preferably less than 45 min. This constitutes a significant advantage compared to casting in hollow moulds in a starch moulding powder, where the gelatin products can usually only be removed after a drying time of from 24 to 72 hours.

In principle any material, in particular plastics material, which is temperature stable (up to approximately 95° C.) and which is suitable for contact with foodstuffs, can be used for the solid hollow moulds. Hollow moulds made of silicone, which on account of its flexibility enables easy demoulding of the gelatin products, are particularly preferred.

Further examples of suitable plastics materials are polycarbonate (PC) or polyethylene terephthalate (PET), for example. Hollow moulds can be produced from thin films of these plastics by means of thermoforming, similarly to the known blister packs for medicinal drugs. These materials are more economical than silicone, which opens up the possibility of producing individualised hollow moulds, for example having inscriptions which are impressed into the gelatin products. These hollow moulds can then be discarded after relatively few product cycles.

Once the gelatin products have been removed from the hollow moulds, they can be either treated with a release wax or dusted with sucrose and/or citric acid, depending on the desired look.

The present invention also relates to gelatin products produced in accordance with the method according to the invention. In spite of their new composition, these products, when consumed, have the typical texture expected of gelatin products by consumers.

As already mentioned in the introduction, the term "gelatin products" within the scope of the present invention includes all confectionery products, dietary supplements, or medicinal products having the corresponding composition, regardless of their external form. Typical examples of such products are gummy sweets, fruit gummies, fortified gummies, chewable tablets, etc.

The gelatin products according to the invention preferably have a dry matter content of at least 78 wt % and/or a water activity ($a_w$ value) of less than 0.75. As already described in conjunction with the casting compound according to the invention, there is no, or only an insignificant increase of the dry matter content during the cooling and setting.

These and further advantages of the invention will be explained in greater detail on the basis of the following examples.

EXAMPLES

Gelatin products were produced in accordance with the method described hereinafter from six different casting compounds according to the invention (Examples 1 to 6) and one casting compound, not according to the invention, as Comparative Example.

For this purpose, the gelatin was firstly dissolved completely in hot water (70 to 80° C.), then sorbitol and as appropriate glycerol was/were added, and the mixture was stirred homogeneously and was heated again to 70 to 80° C.

In parallel, a so-called sugar slurry was produced by boiling glucose syrup, sucrose, and sorbitol (and as appropriate pectin) in water under pressure to at least 125° C. The sugar slurry cooled to approximately 110° C. and the gelatin/sorbitol solution were combined, and the mixture was degassed under vacuum and cooled to 80° C. During the degassing, the water content of the composition was also reduced to such an extent that the dry matter content was at least 78 wt %.

Citric acid was then added as acidifier to the charge, and the casting compound was filled into hollow moulds made of silicone (Examples 1 to 5 and Comparative Example) or into hollow moulds in a PET blister pack (Example 6). For this purpose, a laboratory casting installation from the company Winkler and Dünnebier Süßwarenmaschinen GmbH was used. The filling quantity was in each case between 1 and 5 g.

After a cooling time of at most 60 min. at less than 12° C. ambient temperature, the gelatin products according to the invention (gummy sweets/chewable tablets) could be demoulded. The products can then be lubricated as desired using a release wax or dusted with sugar and citric acid and then packaged.

In Table 1 below, the respective compositions of the finished casting compound prior to filling into the hollow moulds are specified for Examples 1 to 6 and the Comparative Example. Various parameters of the casting compound, the production method, and the produced gelatin products are also specified.

TABLE 1

| | | Comp. Ex. | Ex. 1 | Ex. 2 | Ex. 3 | Ex. 4 | Ex. 5 | Ex. 6 |
|---|---|---|---|---|---|---|---|---|
| Composition of the casting compound in kg | Gelatin (Standard) | 7.3 | — | — | — | — | — | — |
| | Gelatin MW > 130 kDa, proportion > 130 kDa at least 35% | — | 7.3 | 7.3 | 10.0 | 7.0 | 8.4 | 5.5 |
| | Glucose syrup DE 42 | 42.1 | — | — | — | — | — | — |
| | Glucose syrup DE 60 | — | 39.1 | 9.1 | 16.6 | 17.6 | 18.5 | 38.7 |
| | Sucrose | 33.4 | 31.4 | 41.4 | 36.2 | 38.2 | 39.1 | 20.8 |
| | Sorbitol | — | 6.9 | 16.9 | 16.6 | 16.6 | 17.5 | 13.3 |
| | Glycerol | — | — | — | — | — | — | 3.3 |
| | Pectin | — | — | — | — | 0.4 | — | — |
| | Water | 15.3 | 15.3 | 15.3 | 18.7 | 18.7 | 14.4 | 16.3 |
| | Citric acid 50% ig | 2.0 | 2.0 | 2.0 | 2.0 | 2.0 | 2.0 | 2.0 |
| Temperature in ° C. | . . . of the gelatin solution at the time of addition of the sugar slurry | 65 | 70 | 72 | 70 | 70 | 70 | 70 |
| | . . . when boiling the sugar slurry | 125 | 125 | 125 | 125 | 128 | 130 | 130 |
| | . . . of the sugar slurry at the time of addition of the gelatin solution | 110 | 105 | 115 | 110 | 115 | 120 | 110 |
| | . . . of the casting solution after addition of the citric acid | 90 | 80 | 92 | 91 | 83 | 90 | 80 |

TABLE 1-continued

| | Comp. Ex. | Ex. 1 | Ex. 2 | Ex. 3 | Ex. 4 | Ex. 5 | Ex. 6 |
|---|---|---|---|---|---|---|---|
| Dry matter content of the casting compound prior to pouring in wt % | 82 | 81 | 84 | 78 | 78 | 83 | 82 |
| $a_w$ value (25° C.) of the casting compound prior to pouring | Moulding not possible, therefore no products could be produced! | 0.701 | 0.699 | 0.755 | 0.684 | 0.691 | 0.713 |
| Temperature of the feeder head in ° C. | | 88 | 88 | 88 | 88 | 88 | 80 |
| Core temperature after pouring into hollow moulds in ° C. | | n/a | 70 | 67 | 69 | 73 | 71 |
| Water content of the gelatin products in wt % | | 19.6 | 19.7 | 23.0 | 18.8 | 19.5 | 21.3 |
| Dry matter content of the gelatin products in wt % | | 80.4 | 80.3 | 76.9 | 81.2 | 80.5 | 78.7 |
| Bloom strength of the gelatin products in g — after 1 day | | 1019 | 558 | 874 | 985 | 1243 | 420 |
| after 1 week | | 1023 | 839 | 1021 | 1283 | 1538 | 453 |
| after 4 weeks | | 976 | 1098 | 950 | 1830 | 1423 | 507 |

The Comparative Example corresponds to the typical recipe for a mogul installation according to the prior art, with a standard gelatin, low-hydrolysed glucose syrup (DE 42), and without sugar alcohols. This casting compound could be moulded only with difficulty on account of filament formation and air inclusions and was still too soft and too tacky after a cooling time of 60 min. to be removed from the silicone moulds. In the case of the gelatin products according to Example 1, which were produced from a casting compound comprising high-molecular gelatin, highly hydrolysed glucose syrup (DE 60) and sorbitol, these could be removed already after less than 60 min.

In Examples 2 to 5, which contained modified proportions of sucrose, glucose syrup and sorbitol, and also in the case of Example 6 with additional glycerol, a demoulding of the products was possible already after at most 40 min., wherein the end products had different textures in part (for example shorter, more solid texture in the case of Example 4, which additionally contained pectin).

By varying the recipe of the casting compound according to the invention, the texture properties of the produced gelatin products could be modified depending on the dry matter content content, gelatin dosing, and sugar composition.

The invention claimed is:

1. A casting compound for producing gelatin products by pouring into solid hollow moulds, comprising a pourable homogeneous aqueous solution containing the following constituents:
   4 to 16 wt % of gelatin having a mean molecular weight, determined by gel chromatography, of at least 130 kDa, wherein at least 35 wt % of the gelatin has a molecular weight of more than 130 kDa, and wherein the gelatin is obtained from connective tissue or bones of pigs, cattle, or poultry;
   6 to 76 wt % of one or more sugar alcohols;
   8 to 50 wt % of glucose syrup with a viscosity of less than 800 mPa·s, measured with a dry matter content of 80 wt % and at a temperature of 50° C. wherein the glucose syrup has a dextrose equivalent of 50 or more; and
   0 to 50 wt % of sucrose,
wherein the glucose syrup and the sugar alcohol(s) together make up 25 to 76 wt % of the aqueous solution, and wherein the aqueous solution has a dry matter content of at least 78 wt % and a water activity (aw value) of less than 0.75.

2. The casting compound according to claim 1, wherein the homogeneous aqueous solution also contains one or more flavourings, colourings and/or acidifiers.

3. The casting compound according to claim 1, wherein the homogeneous aqueous solution also contains less than 45 wt % of one or more nutrients and/or pharmaceutical active substances.

4. The casting compound according to claim 1, also comprising one or more insoluble constituents, which are dispersed in the aqueous solution.

5. The casting compound according to claim 3, wherein the nutrients are selected from vitamins, minerals, plant extracts and peptides.

6. The casting compound according to claim 1, wherein the gelatin is contained in the aqueous solution in an amount of from 5 to 12 wt %.

7. The casting compound according to claim 1, wherein the aqueous solution contains from 8 to 40 wt % of the glucose syrup.

8. The casting compound according to claim 1, wherein the aqueous solution contains from 15 to 45 wt % of the sucrose.

9. The casting compound according to claim 1, wherein the aqueous solution contains from 10 to 30 wt % of the sugar alcohol(s).

10. The casting compound according to claim 1, wherein the sugar alcohol(s) is/are selected from sorbitol, mannitol, erythritol and glycerol.

11. The casting compound according to claim 1, wherein the homogeneous aqueous solution also comprises one or more further hydrocolloids in an amount of from 0.1 to 10 wt %.

12. The casting compound according to claim 1, wherein the gelatin has a mean molecular weight, determined by gel chromatography, of at least 145 kDa.

13. The casting compound according to claim 1, wherein at least 45 wt % of the gelatin has a molecular weight of more than 130 kDa.

14. The casting compound according to claim 1, wherein the glucose syrup has a viscosity of less than 700 mPa·s.

* * * * *